(12) United States Patent
Ananthan

(10) Patent No.: US 6,465,479 B1
(45) Date of Patent: Oct. 15, 2002

(54) PYRIDOMORPHINANS AND USE THEREOF

(75) Inventor: Subramaniam Ananthan, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 153 days.

(21) Appl. No.: 09/637,934

(22) Filed: Aug. 14, 2000

Related U.S. Application Data

(60) Provisional application No. 60/148,580, filed on Aug. 13, 1999, and provisional application No. 60/210,760, filed on Jun. 12, 2000.

(51) Int. Cl.$^7$ ............... C07D 491/147; A61K 31/4355; A61K 31/436
(52) U.S. Cl. ............... 514/279; 546/39; 546/40
(58) Field of Search ............... 514/279; 546/39, 546/40

(56) References Cited

U.S. PATENT DOCUMENTS

| | | | | |
|---|---|---|---|---|
| 4,816,586 A | * | 3/1989 | Portoghese | 544/340 |
| 5,223,507 A | * | 6/1993 | Dappen et al. | 514/279 |
| 5,811,400 A | * | 9/1998 | Schiller | 514/19 |

FOREIGN PATENT DOCUMENTS

| WO | WO 96/0255 | 2/1996 |
|---|---|---|

OTHER PUBLICATIONS

Subramaniam Ananthan et al., Journal of Medicinal Chemistry, vol. 42, (18) pp. 3527–3538, Published Aug. 19, 1999.*
Ananthan et al., Opioid Receptor Ligands: Synthesis and Structure–Activity Relationships of 4'–Phenyl Pyrido–and Pyrimidoepoxymorphinans, 214$^{th}$ ACS National Meeting, 1997.
Ananthan et al., Synthesis, Opioid Receptor Binding, and Biological Activities of Naltrexone–Derived Pyrido–and Pyrimidomorphinans, *Journal of Medicinal Chemistry*, vol. 42, No. 18, 1999: 3527–3538.
Ananthan et al., Synthesis and Opioid Receptor Binding Profiles of Phenyl Pyridomorphinans, 215$^{th}$ ACS National Meeting, 1998.
Mathews et al., Lack of Antinociceptive Tolerance with SoRI 9409, An Opioid Mu Agonist/Delta Antagonist, Regional Meeting of Southwestern and Rocky Mountain Division of American Association for the Advancement of Sciences, 1999.
Mathews et al., Pharmacological Activities of Naltrexone–Derived Pyrido–and Pyrimidomorphinans, International Narcotics Research Conference, 1999, Abstract Mon41.

* cited by examiner

Primary Examiner—Alan L. Rotman
(74) Attorney, Agent, or Firm—Connolly Bove Lodge & Hutz LLP

(57) ABSTRACT

Compounds represented by the formula:

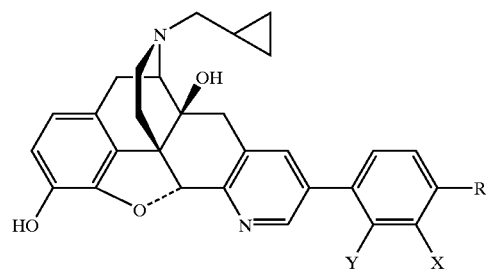

wherein each of Y, X and R individually is H, OH, alkyl, alkoxy, aryl, halo, $CF_3$ and $NO_2$, provided that at least one of Y, X and R is other than H; and pharmaceutically acceptable salts thereof are provided. Compounds of the above formula are useful as analgesics for treating pain, as immunomodulators and for treating drug abuse.

25 Claims, 5 Drawing Sheets

PYRIDOMORPHINANS AND USE THEREOF

This application claims the benefit of provisional application Nos. 60/148,580 filed on Aug. 13, 1999 and 60/210,760 filed Jun. 12, 2000.

FEDERALLY SPONSORED RESEARCH OR DEVELOPMENT

This invention was made under Grant DA 08883 from the National Institute on Drug Abuse.

TECHNICAL FIELD

The present invention relates to certain pyridomorphinan compounds and more particularly to naltrexone-derived pyridomorphinan compounds. Compounds of the present invention exhibit high δ antagonist potency. Moreover, compounds of the present invention possess μ agonist characteristics. Compounds of the present invention are especially useful as analgesics for treating patients suffering from pain. Compounds of the present invention are also suitable for treating drug abuse including cocaine, methamphetamine and opioids such as morphine and heroin abuse. Also, compounds of the present invention can be used as immunomodulatory agents.

BACKGROUND OF INVENTION

Opioid receptors belong to the superfamily of G-protein coupled receptors that mediate the analgesic and other pharmacological actions of morphine and related opioid drugs. In the past, it was believed that only a single opioid binding site existed. The existence of at least three distinct subtypes of opioid receptors, designated up μ, δ and κ receptors, in the central nervous system and periphery is now well established. Human μ, δ and κ receptors have been cloned and have been shown to belong to the G protein-coupled receptor (GPCR) superfamily.

The existence of three distinct opioid receptor types, μ, δ and κ, is confirmed by the recent cloning of these three opioid receptors from mouse, rat and human cDNAs. All three of the opioid receptor types are located in human brain or spinal cord tissues and each has a role in the mediation of pain. Opiates are used extensively for the treatment of pain and are the most effective analgesic agents available. Morphine and its analogues currently prescribed as potent analgesics are μ selective ligands. The general administration of these medications is limited by side-effects such as respiratory depression, depression of gastrointestinal motility and development of tolerance and physical dependence.

The development of potent and selective antagonist and agonist ligands for each of these opioid receptor subtypes has been the goal of medicinal chemists for many years because of their potential usefulness as pharmacological tools and as therapeutic agents. Among the μ, δ and κ receptors, the development of antagonist and agonist ligands acting through the δ receptor has become the focus of research in recent years due to the therapeutic potential of opioid δ ligands. Various studies suggest that δ selective agonists could be potentially useful as analgesics devoid of side effects such as respiratory depression and physical dependence side effects. Selective antagonists of δ receptors have been shown to display immunomodulatory effects as well as modulatory effects on the actions of drugs of abuse such as cocaine and methamphetamines. Moreover, recent studies using rodents have demonstrated that δ opioid antagonists are capable of preventing the development of tolerance and dependence to μ agonist such as morphine without interfering with the μ opioid antinociception.

It has been found that a number of ligands synthetically derived from naltrexone display significant selectivity toward the δ receptors. Among these, the indolomorphinan naltrindole is presently widely used as δ selective antagonist ligand, and other ligands such as its 5'-isothiocyanate derivative, benzofuran analog, and (E)-7-benzylidenenaltrexone have been useful in the pharmacological characterization of δ opioid receptor subtypes.

Continuing efforts exist for developing subtype selective nonpeptide opioid ligands.

SUMMARY OF INVENTION

The present invention relates to compounds represented by the following formula:

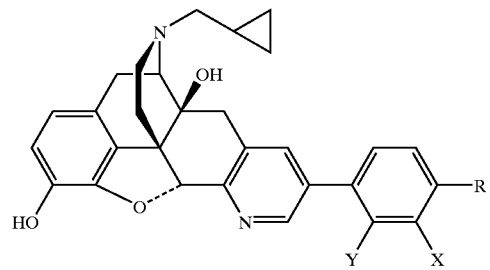

wherein each of Y, X and R is individually selected from the group consisting of hydrogen, hydroxy, alkyl, alkoxy, aryl, halo, $CF_3$ and $NO_2$ provided that at least one of Y, X and R is other than hydrogen; and pharmaceutically acceptable salts thereof.

The present invention also relates to treating a patient suffering from pain which comprises administering to the patient a pain treating effective amount of at least one of the above compounds.

A further aspect of the present invention relates to treating a patient in need of an immunomodulatory agent which comprises administering to the patient an immunomodulatory effective amount of at least one of the above compounds.

A still further aspect of the present invention relates to treating a patient suffering from drug abuse which comprises administering an effective amount for treating drug abuse of at least one of the above compounds.

Still other objects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

Figure 1A:
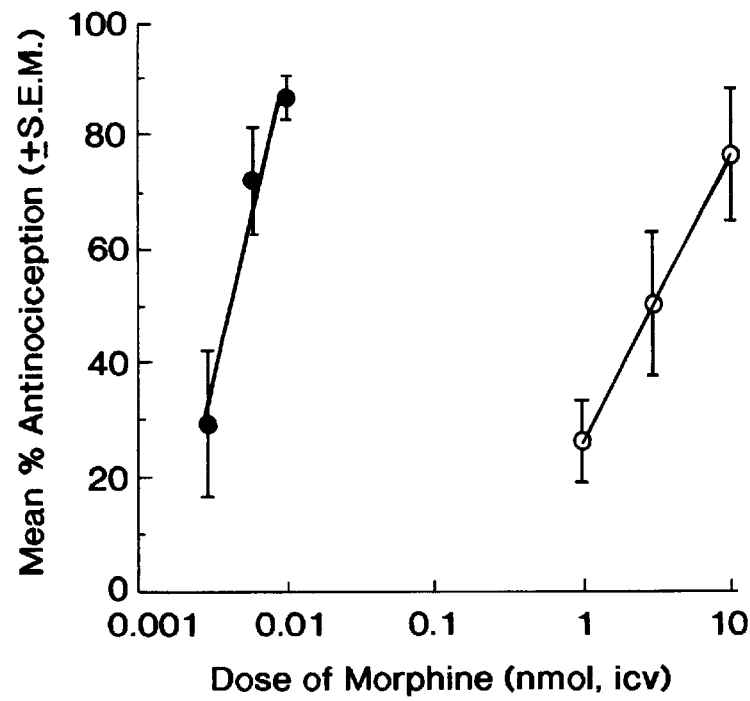
FIG. 1A illustrates antinociceptive dose-response curves for morphine.

The compounds according to the present invention are represented by the following formula:

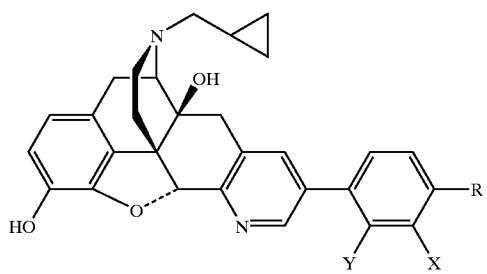

wherein each of Y, X and R is individually selected from the group consisting of hydrogen, hydroxy, alkyl, alkoxy, aryl, halo, $CF_3$ and $NO_2$, provided that at least one of Y, X and R is other than hydrogen; and pharmaceutically acceptable salts thereof.

The alkyl groups typically contain 1 to about 6 carbon atoms, and more typically 1 to about 3 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. Examples of suitable cyclic aliphatic groups typically contain 3–6 carbon atoms and include cyclopentyl and cyclohexyl. Suitable alkoxy groups contain 1–6 carbon atoms and include methoxy, ethoxy, propoxy and butoxy. Examples of aryl groups are phenyl and naphthyl. Examples of halo groups are F, Cl, Br and I.

Pharmaceutically acceptable salts of the compounds of the present invention include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonium.

Some specific compounds according to the present invention are represented by the following combinations of R, X and Y groups:

| R | X | Y |
|---|---|---|
| F | H | H |
| Br | H | H |
| I | H | H |
| $CH_3$ | H | H |
| $CH_3O$ | H | H |
| $CF_3$ | H | H |
| $NO_2$ | H | H |
| OH | H | H |
| $C_6H_5$ | H | H |
| H | Cl | H |
| H | H | Cl |

-continued

| R | X | Y |
|---|---|---|
| Cl | Cl | H |
| Cl | H | Cl |
| Cl | H | H |
| Cl | Cl | Cl |

The preferred compound according to the present invention is represented by R being Cl, X being H and Y being H and referred to a 5'-(4-chlorophenyl)-17-(cyclopropylmethyl)-6,7-didehydro-3,14-dihydroxy-4,5 α-epoxypyrido[2',3':6,7]morphinon (also referred to herein as compound "6d").

Compounds of the present invention can be synthesized from naltrexone by condensation with, for instance, a substituted phenyl malondialdehyde and ammonium acetate in refluxing acetic acid. By way of example, a preferred compound of the present invention can be produced by the following scheme:

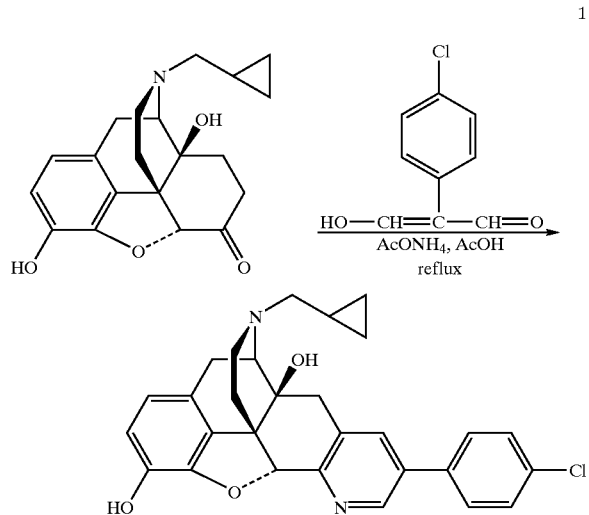

The following non-limiting examples are presented to further illustrate the present invention.

EXAMPLE 1

Preparation of 5'-(4-Chlorophenyl)-17-(Cyclopropylmethyl)-6,7-didehydro-3,14-dihydroxy-4,5α-epoxypyrido[2'3':6,7]morphinan (6d)

A stirred mixture of naltrexone hydrochloride (4.72 g, 12.5 mmol), 2-(4-chlorophenyl)malondialdehyde (2.5 g, 13.7 mmol), and ammonium acetate (1.93 g, 25 mmol) in AcOH (75 mL) was heated to reflux in an oil bath at 130–135° C. under an argon atmosphere until TLC analysis of the reaction mixture using EtOAc:cyclohexane:$Et_3N$ (1:1:0.02) as the solvent system indicated complete disappearance of naltrexone (approximately 20 h). The reaction mixture was cooled to room temperature, and the solvent was removed under reduced pressure. The residue was treated with water, and the pH of the mixture was adjusted to 8 with saturated aqueous $NaHCO_3$. The solid that separated was collected by filtration and dried. The crude product was chromatographed over a column of silica, using $CHCl_3$-MeOH (98:2) as the eluent, and then recrystallized from EtOAc/cyclohexane to give 6d (2.12 g, 35%): mp>175° C. dec; TLC $R_f$ 0.45 ($CHCl_3$-MeOH, 97:3); $^1H$ NMR ($CDCl_3$) δ0.15–0.19 and 0.56–0.61 (2m, 4H, cyclopropyl $CH_2CH_2$), 0.83–0.93 (m, 1H, cyclopropyl CH), 1.81–1.88 (m, 1H, C-15 H), 2.33–2.53 (m, 4H, C-15 H, C-16 H and NCH$_2$-cyclopropyl), 2.61–2.84 (m, 4H, C-8 H$_2$, C-10 H and C-16 H), 3.17 (app d, 1H, J=18.6 Hz, C-10 H), 3.31 (app d, 1H, J=6.3 Hz, C-9 H), 4.5–5.5 (broad hump, 2H, C-3 OH and C-14 OH), 5.59 (s, 1H, C-5H), 6.59 and 6.68 (AB-System, 2H, J=8.1 Hz, C-1 H and C-2 H), 7.38–7.44 (m, 4H, C-2"H, C-3" H, C-5" and C-6" H), 7.48 (d, 1H, J=2.2 Hz, C-4' H), 8.69 (d, 1H, J–1.9 Hz, C-6' H); MS m/z 487 (MH)$^+$ Anal. (C$_{29}$H$_{27}$ClN$_2$O$_3$), C, H, N, Cl.

EXAMPLE 2
Opioid Receptor Binding and Bioassays in Smooth Muscle Preparations The binding affinities of compound 6d for the $\mu$ and $\delta$ receptors were determined by inhibition of binding of [$^3$H] DAMGO and [$^3$H]DADLE to rat brain membranes. The affinity of 6d for the $\kappa$ receptors was determined by inhibition of binding of [$^3$H]U69,593 to guinea pig brain membranes. The $\delta$, $\mu$ and $\kappa$ opioid receptor binding affinities along with binding selectivity ratios are given in Table 1. The opioid agonist and antagonist potencies were determined on the electrically stimulated mouse vas deferens (MVD) and guinea pig ileum (GPI) smooth muscle preparations. The opioid antagonist and agonist potencies in the MVD and GPI are listed in Table 2.

TABLE 1

Opioid Receptor Binding Affinities in Homogenates of Rat or Guinea Pig Brain Membranes

| | K$_i$ (nM) ± SEM | | | Selectivity Ratio | |
|---|---|---|---|---|---|
| cmpd | $\delta^a$ | $\mu^b$ | K$_i^c$ | $\mu/\delta$ | K$_i/\delta$ |
| 6d | 2.2 ± 0.16 | 51.0 ± 8.0 | 20.0 ± 1.04 | 23 | 9.1 |
| naltrexone | 39.5 ± 3.0 | 2.5 ± 0.21 | 7.0 ± 0.18 | 0.06 | 0.18 |
| naltrindole | 0.41 ± 0.09 | 99 ± 4.6 | 35.8 ± 4.0 | 241 | 87 |

[a]Displacement of [$^3$H]DADLE (1.3–2.0 nM) in rat brain membranes using 100 nM DAMGO to block binding to $\mu$ sites.
[b]Displacement of [$^3$H]DAMGO (1.4–3.0 nM) in rat brain membranes.
[c]Displacement of [$^3$H]U69,593 (1.2–2.2 nm) in guinea pig brain membranes.

presence of 1 $\mu$M CTAP, a $\mu$ opioid selective antagonist, the dose-response curve of 6d in the GPI was shifted rightward 5.1-fold. Testing in the presence of nor-BNI, a $\kappa$ opioid selective antagonist, shifted the dose-response curve 1.6-fold rightward. At 1 $\mu$M concentration, the nonselective opioid receptor antagonist naloxone shifted the dose-response curve 5.2-fold to the right. These data show that the agonist activity of 6d in the GPI is mediated through the opioid $\mu$ receptors.

EXAMPLE 3
Pharmacological Evaluations in Animals

In the following examples, male ICR mice(20–30 grams) were used. Solutions of compound 6d and U69,593[(5$\alpha$, 7$\alpha$, 8$\beta$)-(+)-N-methyl-N-(5 7-(1-pyrrolidinyl)-1-oxaspiro(4,5) dec-8-yl)-benzeneacetamide] were prepared by initially dissolving compound 6d and U69,593 in 100 $\mu$l of glacial acetic acid and 900 $\mu$l of distilled water. The solution was brought up to approximately pH 5.5 with 1.74 M NaOH and then the final volume adjusted with distilled water. Vehicle was prepared in a similar fashion without the drug. Additional compounds used in these studies were dissolved in distilled water (i.c.v. injections) or physiological saline (i.p. injections).

Antinociception was assessed using either the 55° C. warm-water tail-flick test or the acetic-acid writhing assay. For the tail-flick test, the latency to the first sign of a rapid tail-flick was taken as the behavioral endpoint (Jannsen et al., The inhibitor effects if fentanyl and other morphine-like analgesics on the warm water-induced tail-withdrawal reflex in rats. *Arzneimittel-Forschung* 13:502–505,1963). Each mouse was first tested for baseline latency by immersing its tail in the water and recording the time to response. Mice not responding within 5 sec were excluded from further testing. Mice were then administered the test compound and tested for antinociception at 10, 20, 30, 45, 60 and 90 min post-injection. A maximum score was assigned (100%) to animals not responding within 15 sec to avoid tissue damage. Antinociception was calculated by the following formula: % antinociception=100×(test latency-control latency)/(15-control latency). For the acetic acid writhing test, mice were injected i.p. with 0.9% acetic acid. They were then placed in a clear Plexiglas observation jar and the number of abdominal writhes recorded for 15 min (Mogil et al., Heritability of nociception I: responses of 11 inbred mouse

TABLE 2

Opioid Antagonist and Agonist Potencies in the MVD and GPI Preparations

| | antagonist activity | | | | | agonist activity | |
|---|---|---|---|---|---|---|---|
| | DPDPE ($\delta$)$^a$ | | PL-017 ($\mu$)$^b$ | | K$_e$ selectivity | MVD IC$_{50}$ (nM) or % | GPI IC$_{50}$ (nM) or % |
| compd | IC$_{50}$ ratio | K$_e$ (nM)$^c$ | IC$_{50}$ ratio | K$_e$ (nM)$^c$ | ratio $\mu/\delta$ | max resp$^d$ | max resp$^d$ |
| 6d | 1519 ± 797 | 0.66 | $^e$ | | | 21% | 163 ± 22 |
| nactrindole$^f$ | 2000 ± 400 | 0.49 | 24 ± 2 | 43 | 88 | 16% | 18 |

[a]DPDPE in the MVD preparation.
[b]PL-017 in the GPI preparation.
[c]K$_e$ (nM) = [antagonist]/(IC$_{50}$ ratio - 1), where the IC$_{50}$ ratio is the IC$_{50}$ of the agonist in the presence of antagonist divided by the control IC$_{50}$ in the same preparation (n ≧ 3).
[d]Partial agonist activity is expressed as the percentage inhibition of contraction at a concentration of 1 $\mu$M.
[e]The agonist effects precluded the determination of antagonist effects.
[f]Data from published sources.

The above results show that the chlorophenyl compound 6d displays relatively potent $\delta$ antagonist activity with a K$_e$ of 0.66 nM. Surprisingly, 6d functioned as a full agonist in the GPI with an IC$_{50}$ of 163 nM (0.64×morphine) In the strains on 12 measures of nociception. *Pain* 80:67–82,1999). Percent antinociception was calculated using the formula: % MPE (maximum possible effect)=100-((#writhes individual mouse/mean # writhes control group)×100).

To further determine the in vivo opioid receptor profile of compound 6d, mice were pretreated with a mu (β-FNA, 19 nmol, i.c.v., −24 hr), delta (naltrindole, 20 mg/kg, i.p., −20 min) or kappa (nor-BNI, 1 nmol, i.c.v., −24 hr) selective antagonist. Control mice received a vehicle injection (5 µl distilled water, i.c.v., −24 hr). These times and doses have previously been shown to produce selective blockade of mu, delta and kappa receptors, respectively (Portoghese et al., Naltrindole, a highly selective and potent non-peptide delta opioid receptor antagonist. *Eur J Pharmacol* 146:185–186, 1988; Jiang et al., Naltrindole, a highly selective and potent non-peptide delta opioid receptor antagonist. *Eur J Pharmacol* 146:185–186, 1991; Horan et al., Extremely long-lasting antagonistic actions of nor-binaltorphimine (nor-BNI) in the mouse tail-flick test. *J Pharmacol Exp Ther* 260:1237–1243, 1992). Mice then received an $A_{90}$ dose of compound 6d (30 nmol, i.c.v.) followed 10 min later by an i.p. injection of 0.9% acetic acid.

To determine antagonist actions, mice were pretreated with vehicle or various doses of compound 6d (i.p., −20 min) followed by injection of i.c.v. $A_{90}$ doses of selective mu [D-Ala$^2$, NMPhe$^4$, Gly-ol]enkephalin (DAMGO, 0.1 nmol), delta-1 cyclic[D-Pen$^2$, D-Pen$^5$]-enkephalin where Pen is penicillamine (DPDPE, 30 nmol), delta-2 ([D-Ala$^2$, Glu$^4$] deltorphin (20 nmol), or kappa (U69,593, 60 nmol) agonists at 0 min. Antinociception was assessed 10 min after agonist injection, which corresponded to the time of agonist peak effect (Horan et al., 1992).

To test for acute physical dependence on morphine, an acute assay in mice was used (Bilsky et al., Effects of neutral and negative antagonists and protein kinase inhibitors on acute morphine dependence and antinociceptive tolerance in mice. *J Pharmacol Exp Ther* 277: 484–490,1996; Yano et al., Inhibition by naloxone of tolerance and dependence in mice treated acutely and chronically with morphine. *Res Commun Chem Pathol Pharmacol* 16:721–734,1977). Mice were pretreated with morphine (100 mg/kg s.c.) followed four hours later by an injection of the opioid antagonist naloxone (10 mg/kg, i.p.), Compopund 6d (10 mg/kg i.p.) or a combination of both. Mice were immediately placed in a clear Plexiglas cylinder and observed for 15 minutes. The number of vertical jumps was recorded during this time.

Figure 1B:
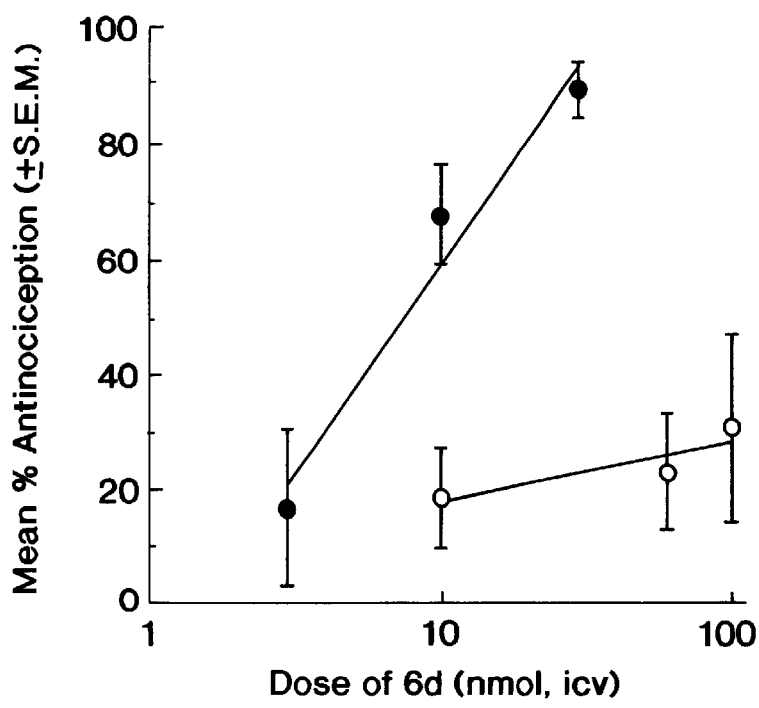
FIG. 1B illustrates antinociceptive dose-response curves for compounds of the present invention.
Figure 2A:
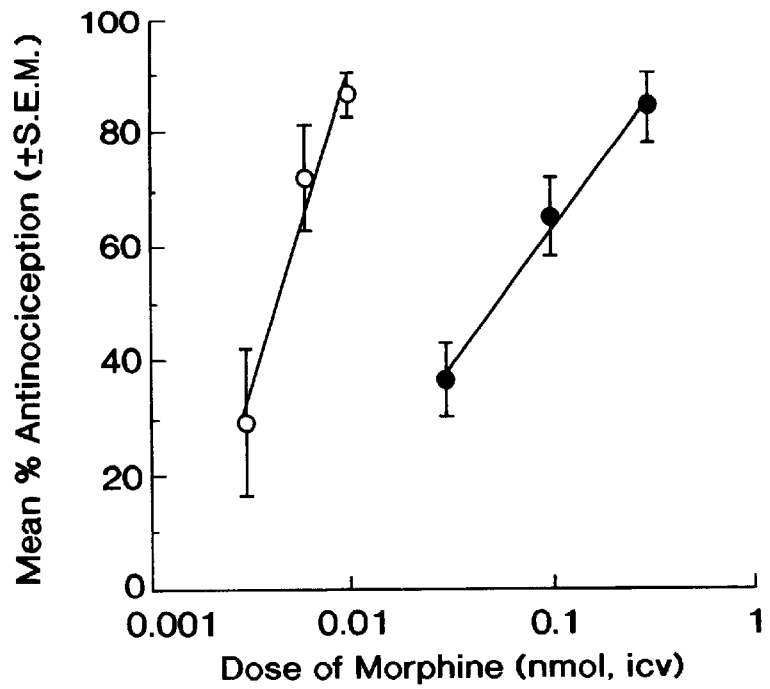
FIG. 2A illustrates tolerance effects of morphine.
Figure 2B:
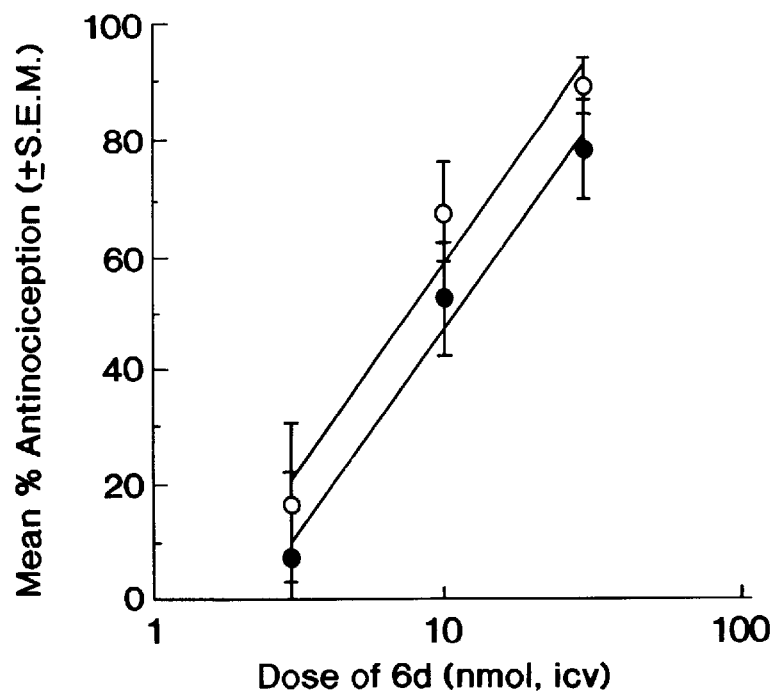
FIG. 2B illustrates tolerance effects of compounds of the present invention.

Compound 6d was evaluated for antinociceptive activity in mice. In the 55° C. tail-flick test (high-intensity stimulus) compound 6d, administered by intracerebroventricular (icv) injections, was a partial agonist with an $A_{50}$ value greater than 100 nmol (FIG. 1b) In the acetic acid writhing assay, 6d displayed full agonist activity with a calculated $A_{50}$ value of 7.5 nmol. Morphine, a prototypic µ agonist, produced a full agonist effect following icv injection in both the 55° C. tail-flick and acetic acid writhing assays (FIG. 1a). The calculated $A_{50}$ values for morphine were 2.94 nmol in the tail-flick and 0.004 nmol in the acetic acid writhing assays. Using a standard tolerance regimen, repeated icv injections of an $A_{90}$ dose of morphine (×2 daily for 3 days) produced a significant rightward shift in the antinociceptive dose-response curve (12.5-fold), indicating the development of tolerance (FIG. 2a). Repeated icv injections of an $A_{90}$ dose of 6d on the other hand did not produce a significant rightward shift (<1.5-fold) in the antinociceptive dose-response curve (FIG. 2b). This indicates that compound 6d may produce limited or no antinociceptive tolerance. The lack of development of tolerance to the antinociceptive effects of 6d may be related to the mixed µ agonist/δ antagonist profile of this compound. The calculated $A_{50}$ values and 95% confidence intervals for each compound and route of administration are summarized in Table 3 below.

TABLE 3

Summary of Antinociceptive activity of morphine and Compound 6d in control mice and mice injected repeatedly (× 2 daily, 3 days) with $A_{90}$ doses of morphine or Compound 6d.

| Drug and Route | Control $A_{50}$ (95% C.I.) | Repeated Injections $A_{50}$ (95% C.I.) | Tolerance Shift |
|---|---|---|---|
| Morphine i.c.v. | 0.004 nmol (0.003–0.006 nmol)† | 0.05 nmol (0.03–0.08 nmol)† | 12.5 |
| 6d i.c.v. | 7.5 nmol (5.3–10.5 nmol)† | 10.9 nmol (7.2–16.5 nmol)† | 1.45 |
| Morphine i.p. | 2.2 mg/kg (1.8–2.7 mg/kg) | 4.78 mg/kg (3.7–6.2 mg/kg) | 2.17 |
| 6d i.p. | 4.6 mg/kg (2.5–8.6 mg/kg) | 3.85 mg/kg (0.9–16.0 mg/kg) | 0.84 |

The calculated $A_{50}$ values for morphine in the tail flick assay by i.c.v. and i.p. routes (and 95% confidence intervals) were 1.7 nmol (0.8–3.7 nmol) and 8.0 mg/kg (6.3–10.0 mg/kg), respectively. In contrast, Compound 6d produced only partial agonist effects following i.c.v. administration (40.3% MPE @ 100 nmol) and had no measurable antinociceptive effect following i.p. administration at doses up to 60 mg/kg in the tail flick assay. In the acetic acid writhing test, both compounds produced full agonist effects following i.c.v. or i.p. administration.

Figure 3A:
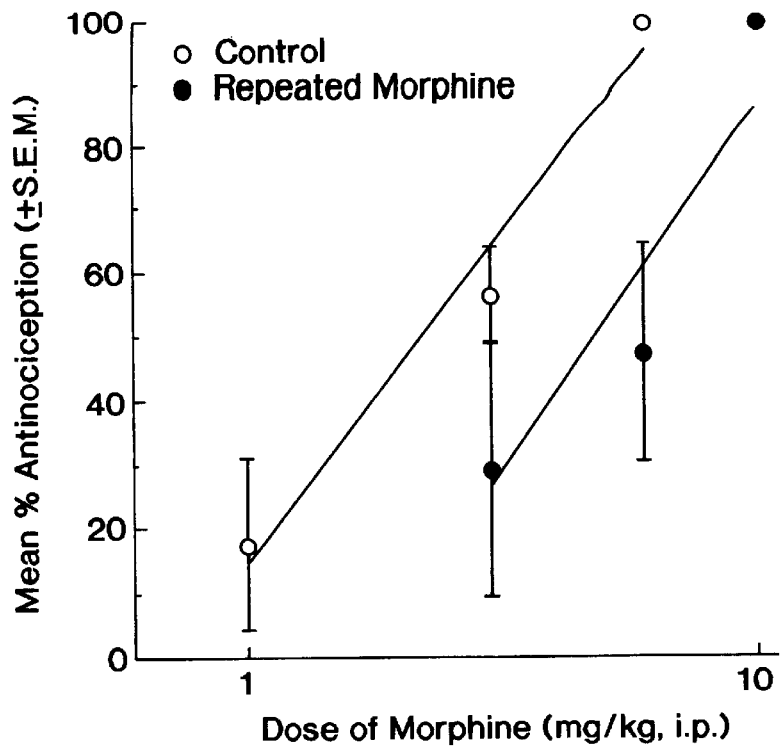
FIG. 3A illustrates antinociceptive dose-response curves for morphine.
Figure 3B:
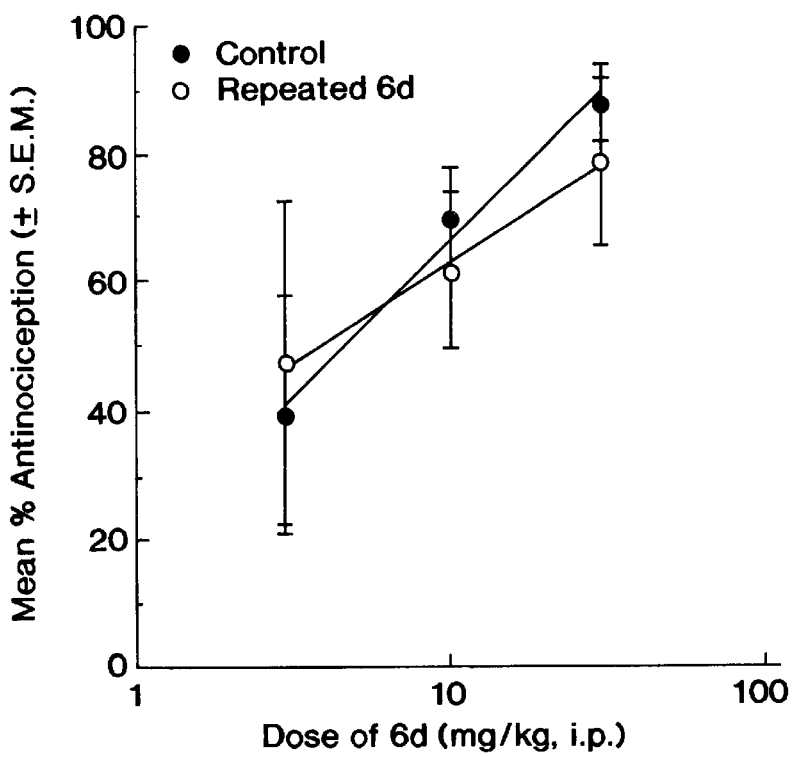
FIG. 3B illustrates antinociceptive dose-response curves for compounds of the present invention.

Repeated administration by i.p. route of approximate $A_{90}$ doses of morphine (6 mg/kg, i.p., ×2 daily for 3 days) shifted the morphine dose-response curve approximately 2.2-fold (FIG. 3a, Table 3). In contrast, repeated injections by i.p. route of $A_{90}$ doses of Compound 6d (30 mg/kg, i.p., ×2 daily for 3 days) did not significantly shift the Compound 6d dose-response curve (FIG. 3b, Table 3).

Figure 4:
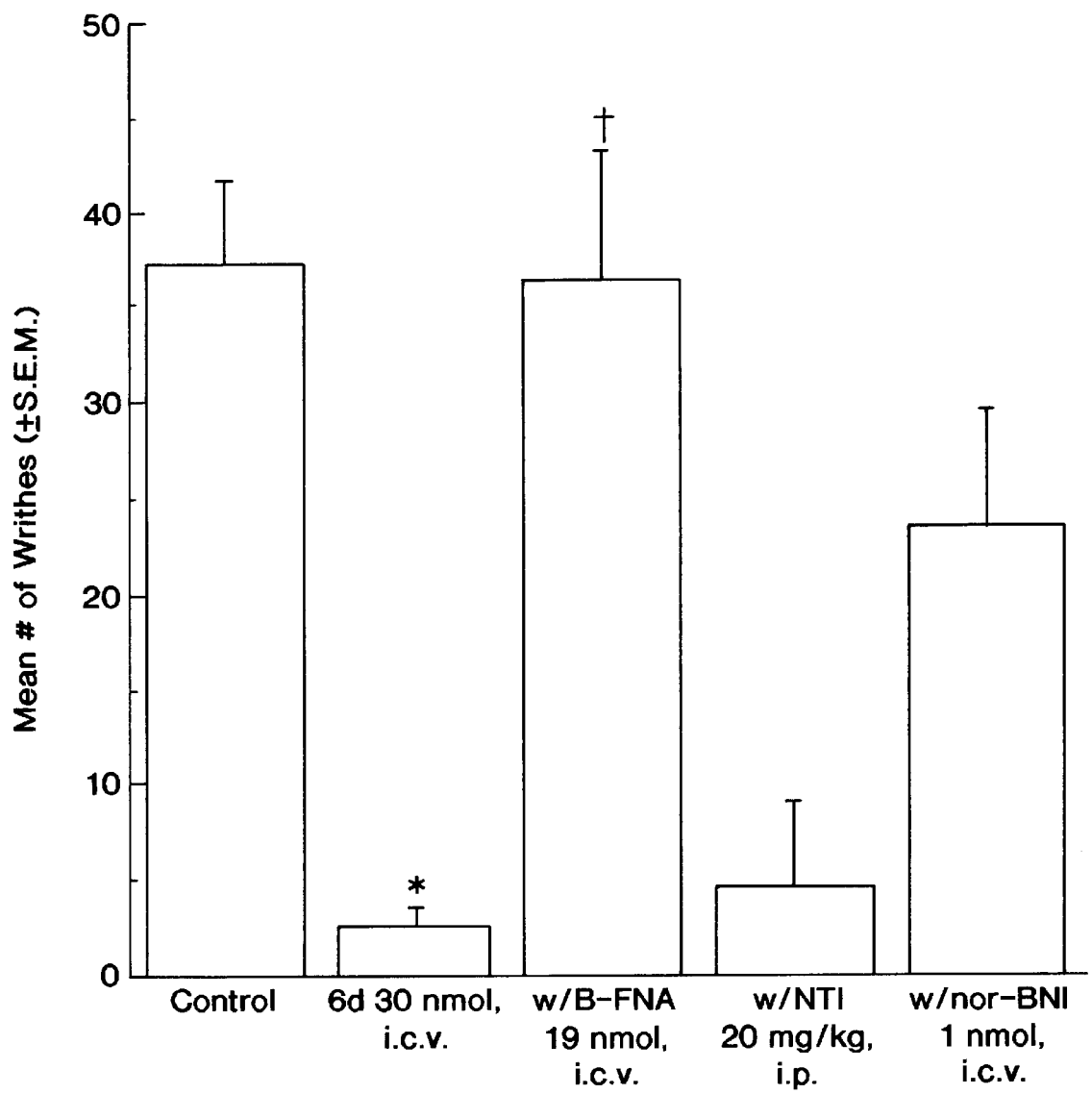
FIG. 4 illustrates nociceptive responses for compounds of the present invention with or without compounds outside the scope of the present invention.

To determine the opioid receptor(s) through which Compound 6d produces its antinociceptive actions, mice were pretreated with vehicle or a selective mu, delta or kappa antagonist. Mice were then injected with an $A_{90}$ i.c.v. dose of Compound 6d and antinociception was assessed in the acetic acid writhing assay. An ANOVA of the data depicted in FIG. 4 yielded an F(4,65)=11.2, p<0.001. Post-hoc analysis using a Scheffé test indicated that the 30 nmol dose of Compound 6d significantly decreased the number of writhes (p<0.001). This effect was blocked by pre-treatment with β-FNA (p<0.002) but not by naltrindole (p>0.99) or nor-BNI (p>0.13). There was also no difference between the vehicle control and nor-BNI group (p>0.23).

Figure 5:
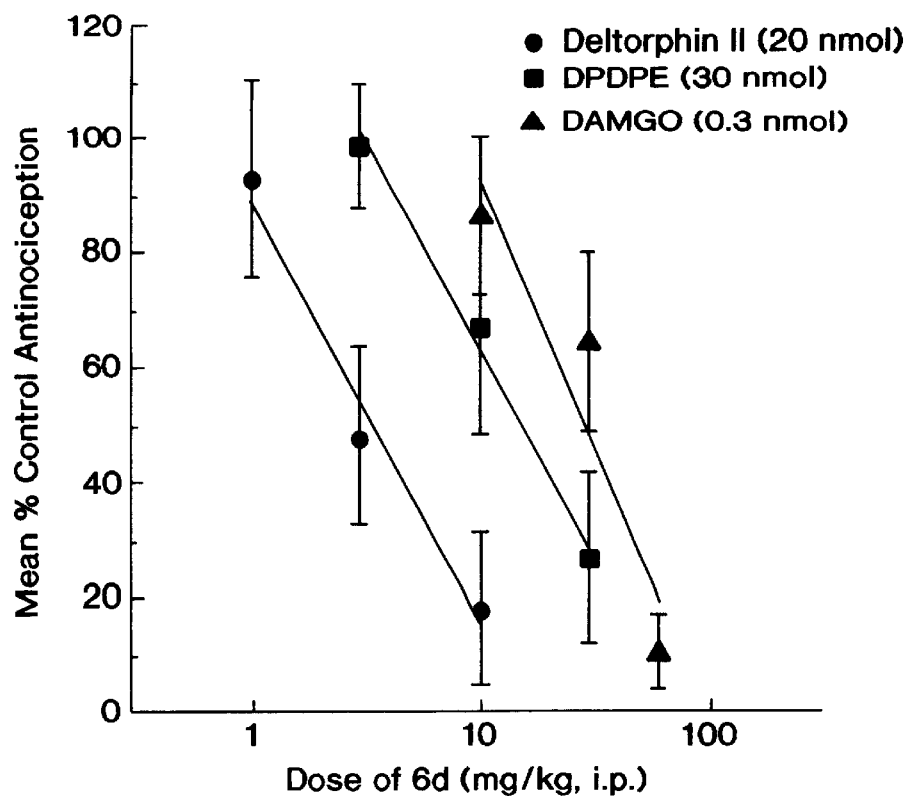
FIG. 5 illustrates antinociceptive dose-response curves for compounds of the present invention in the presence of compounds not within the scope of the present invention.

The antagonist actions of Compound 6d were assessed by pre-treating mice i.p. with doses of Compound 6d. Mice were then injected with $A_{90}$ doses of selective mu, delta or kappa agonists and antinociception was assessed in the 55° C. tail-flick test. The antagonist dose-response curves are depicted in FIG. 5 with the corresponding $ID_{50}$ values and 95% confidence limits displayed in Table 4 below. Compound 6d potently antagonized the actions of the delta-2 selective agonist [D-Ala$^2$, Glu$^4$]deltorphin. The compound was much less potent at antagonizing the actions of the delta-1 agonist DPDPE or the mu agonist DAMGO. In addition, doses of up to 60 mg/kg of Compound 6d did not affect the antinociception actions of the kappa agonist U69, 593.

TABLE 4

Summary of i.p. Compound 6d $ID_{50}$ values against the antinociceptive actions of $A_{90}$ doses of selective opioid agonists

| Agonist | Compound 6d $ID_{50}$ (mg/kg) | 95% Confidence Limits (mg/kg) |
| --- | --- | --- |
| [D-Ala$^2$, Glu$^4$]deltorphin | 3.4 | 2.0–5.8 |
| DPDPE | 15.3 | 8.9–26.4 |
| DAMGO | 28.9 | 20.1–41.5 |
| U69, 593 | >60 | N.D. |

Figure 6:
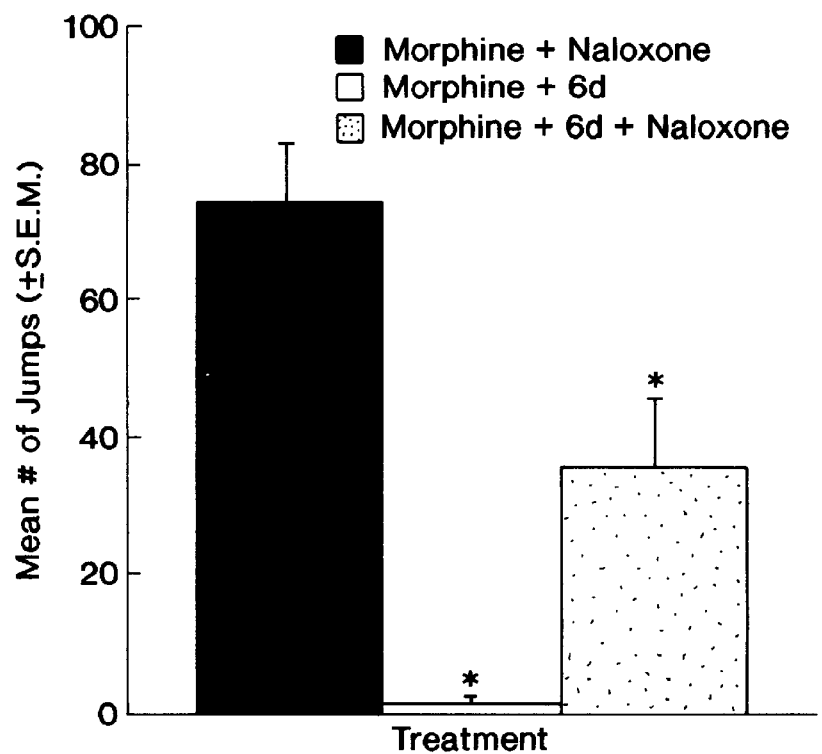
FIG. 6 illustrates opioid withdrawal with compounds of the present invention compared to compounds not within the scope of the present invention.

The ability of Compound 6d to elicit a withdrawal syndrome in morphine (100 mg/kg, i.p., −4 hr) pretreated mice and to attenuate a naloxone precipitated withdrawal (FIG. 6) was determined. An ANOVA yielded an $F(2,56)=11.9$, $p<0.0001$. Post-hoc analysis (Scheffé test) indicated that an i.p. injection of Compound 6d (10 mg/kg) precipitated significantly less vertical jumps than naloxone injection (10 mg/kg, i.p.) ($p<0.001$). Coadministration of Compound 6d and naloxone also produced significantly less jumps than naloxone alone ($p<0.05$).

The above tests demonstrate that compound 6d possesses high binding potency at the δ receptor, high δ antagonist potency in bioassays in the MVD, and moderate μ agonist potency in the GPI. In the antinociceptive studies, 6d displayed partial agonist activity in the tail-flick assay and a full agonist activity in the acetic acid writhing assay. This compound, possessing mixed μ agonist/δ antagonist properties, did not induce tolerance to its antinociceptive effects and did not display any overt signs of toxicity in mice in the dose ranges tested.

Moreover, Compound 6d attenuated opioid withdrawal in mice made acutely dependent on morphine.

The pharmaceutically acceptable effective dosage of the active compound of the present invention to be administered is dependent on the species of the warm-blooded animal (mammal), the body weight, age and individual condition, and on the form of administration.

The pharmaceutical composition may be oral, parenteral, suppository or other form which delivers the compounds used in the present invention into the bloodstream of a mammal to be treated. The preferred method of administration is by i.p. (intraperitoneal) administration since the most effective results were achieved by this route.

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) typically contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A compound represented by the formula:

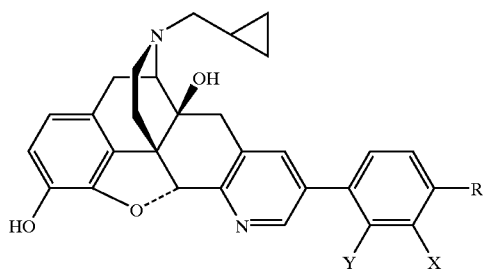

wherein each of Y, X and R individually is selected from the group consisting of hydrogen, hydroxy, alkyl, alkoxy, aryl, halo, $CF_3$ and $NO_2$, provided that at least one of Y, X and R is other than hydrogen; and pharmaceutically acceptable salts thereof.

2. The compound of claim 1 wherein X is H, Y is H and R is Cl.

3. The compound of claim 1 wherein X is H, Y is H and R is F.

4. The compound of claim 1 wherein X is H, Y is H and R is Br.

5. The compound of claim 1 wherein X is H, Y is H and R is I.

6. The compound of claim 1 wherein X is H, Y is H and R is $CH_3$.

7. The compound of claim 1 wherein X is H, Y is H and R is $OCH_3$.

8. The compound of claim 1 wherein X is H, Y is H and R is $CF_3$.

9. The compound of claim 1 wherein X is H, Y is H and R is $NO_2$.

10. The compound of claim 1 wherein X is H, Y is H and R is OH.

11. The compound of claim 1 wherein X is H, Y is H and R is phenyl.

12. The compound of claim 1 wherein X is Cl, Y is H and R is H.

13. The compound of claim 1 wherein X is H, Y is Cl and R is H.

14. The compound of claim 1 wherein X is Cl, Y is H and R is Cl.

15. The compound of claim 1 wherein X is H, Y is Cl and R is Cl.

16. The compound of claim 1 wherein X is Cl, Y is Cl and R is Cl.

17. A method for treating a patient suffering from pain which comprises administering to the patient a pain treating effective amount of at least one compound according to claim 1.

18. The method of claim 17 wherein the administering is i.p. administering.

19. A method for treating a patient in need of an immunomodulatory agent which comprises administering to the patient an immuno-modulatory effective amount of at least one compound according to claim 1.

20. The method of claim 19 wherein the administering is i.p. administering.

21. A method for treating a patient suffering from drug abuse which comprises administering to the patient an effective amount for treating drug abuse of at least one compound according to claim 1.

22. The method of claim 21 in which the drug abuse comprises cocaine or methamphetamine abuse.

23. The method of claim 21 wherein the drug abuse comprises opioid drug abuse.

24. The method of claim 23 wherein the drug abuse comprises heroin or morphine drug abuse.

25. The method of claim 21 wherein the administering is i.p. administering.

* * * * *